(12) United States Patent
Jadhav (10) Patent No.: US 9,687,294 B2
(45) Date of Patent: Jun. 27, 2017

(54) DEPLOYMENT MECHANISM FOR SURGICAL INSTRUMENTS

(71) Applicant: COVIDIEN LP, Mansfield, MA (US)

(72) Inventor: Amarsinh D. Jadhav, Dist-Sangli (IN)

(73) Assignee: COVIDIEN LP, Mansfield, MA (US)

( * ) Notice: Subject to any disclaimer, the term of this patent is extended or adjusted under 35 U.S.C. 154(b) by 270 days.

(21) Appl. No.: 14/543,121

(22) Filed: Nov. 17, 2014

(65) Prior Publication Data

US 2016/0135870 A1     May 19, 2016

(51) Int. Cl.
| | | |
|---|---|---|
| A61B 18/14 | (2006.01) | |
| A61B 17/29 | (2006.01) | |
| A61B 18/00 | (2006.01) | |
| A61B 17/00 | (2006.01) | |

(52) U.S. Cl.
CPC ...... *A61B 18/1445* (2013.01); *A61B 2017/00393* (2013.01); *A61B 2017/00407* (2013.01); *A61B 2017/2923* (2013.01); *A61B 2018/0063* (2013.01); *A61B 2018/00202* (2013.01); *A61B 2018/00208* (2013.01); *A61B 2018/00428* (2013.01); *A61B 2018/00607* (2013.01); *A61B 2018/1422* (2013.01); *A61B 2018/1455* (2013.01); *A61B 2018/1475* (2013.01)

(58) Field of Classification Search
CPC .. A61B 2018/00208; A61B 2018/00428; A61B 2018/00607; A61B 2018/0063; A61B 2018/1422; A61B 2018/1455; A61B 2018/1475; A61B 2018/145; A61B 2018/1452; A61B 2018/1457; A61B 18/1442; A61B 18/1445; A61B 18/1447; A61B 18/146; A61B 18/1462

See application file for complete search history.

(56) References Cited

U.S. PATENT DOCUMENTS

| | | |
|---|---|---|
| 5,312,391 A | 5/1994 | Wilk |
| 5,318,589 A | 6/1994 | Lichtman |
| 5,324,254 A | 6/1994 | Phillips |
| 5,401,274 A | 3/1995 | Kusunoki |
| 5,445,638 A | 8/1995 | Rydell et al. |
| 5,458,598 A | 10/1995 | Feinberg et al. |

(Continued)

FOREIGN PATENT DOCUMENTS

EP     2679176 A1     1/2014

OTHER PUBLICATIONS

Extended European Search Report issued in corresponding application No. 15191287.0 on Apr. 12, 2016.

*Primary Examiner* — Daniel Fowler (57) ABSTRACT

A surgical instrument includes an end effector assembly and a deployment mechanism for deploying a proximal hub associated with an energizable member between proximal and distal positions. The deployment mechanism includes a rotatable shaft, a cord including a proximal end engaged to the rotatable shaft and a distal end engaged to the proximal hub, a biasing member positioned to bias the proximal hub towards the distal position, and a gear assembly operably coupled to the rotatable shaft. The gear assembly is configured to move the proximal hub from the distal position to the proximal position against the bias of the biasing member by rotating the rotatable shaft relative to the cord to at least partially wind-up the cord about the rotatable shaft.

18 Claims, 5 Drawing Sheets

(56) References Cited

U.S. PATENT DOCUMENTS

| | | |
|---|---|---|
| 5,556,397 A | 9/1996 | Long et al. |
| 5,735,873 A | 4/1998 | MacLean |
| 5,792,164 A | 8/1998 | Lakatos et al. |
| 5,893,863 A | 4/1999 | Yoon |
| 5,919,202 A | 7/1999 | Yoon |
| 6,113,596 A | 9/2000 | Hooven et al. |
| 6,156,009 A | 12/2000 | Grabek |
| 6,190,386 B1 | 2/2001 | Rydell |
| 6,270,497 B1 | 8/2001 | Sekino et al. |
| 6,299,625 B1 | 10/2001 | Bacher |
| 6,387,094 B1 | 5/2002 | Eitenmuller |
| 6,551,313 B1 | 4/2003 | Levin |
| 6,679,882 B1 | 1/2004 | Kornerup |
| 6,808,525 B2 | 10/2004 | Latterell et al. |
| 6,942,662 B2 | 9/2005 | Goble et al. |
| 7,033,356 B2 | 4/2006 | Latterell et al. |
| 7,063,699 B2 | 6/2006 | Hess et al. |
| 7,128,254 B2 | 10/2006 | Shelton, IV et al. |
| 7,232,440 B2 | 6/2007 | Dumbauld et al. |
| 7,367,976 B2 | 5/2008 | Lawes et al. |
| 7,402,162 B2 | 7/2008 | Ouchi |
| 7,445,621 B2 | 11/2008 | Dumbauld et al. |
| 7,510,562 B2 | 3/2009 | Lindsay |
| 7,588,570 B2 | 9/2009 | Wakikaido et al. |
| 7,658,311 B2 | 2/2010 | Boudreaux |
| 7,758,577 B2 | 7/2010 | Nobis et al. |
| 7,815,636 B2 | 10/2010 | Ortiz |
| 7,819,872 B2 | 10/2010 | Johnson et al. |
| 8,257,352 B2 | 9/2012 | Lawes et al. |
| 8,353,437 B2 | 1/2013 | Boudreaux |
| 2002/0049442 A1 | 4/2002 | Roberts et al. |
| 2004/0236326 A1 | 11/2004 | Schulze et al. |
| 2005/0187547 A1 | 8/2005 | Sugi |
| 2007/0043352 A1* | 2/2007 | Garrison ............... A61B 18/00 606/51 |
| 2007/0225754 A1 | 9/2007 | Measamer et al. |
| 2008/0077154 A1* | 3/2008 | Edwards ............... A61B 17/683 606/105 |
| 2008/0215050 A1 | 9/2008 | Bakos |
| 2009/0125026 A1 | 5/2009 | Rioux et al. |
| 2009/0125027 A1 | 5/2009 | Fischer |
| 2009/0131974 A1 | 5/2009 | Pedersen et al. |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0292690 A1 | 11/2010 | Livneh |
| 2011/0004209 A1 | 1/2011 | Lawes et al. |
| 2011/0087218 A1 | 4/2011 | Boudreaux et al. |
| 2011/0130757 A1 | 6/2011 | Horlle et al. |
| 2011/0264093 A1 | 10/2011 | Schall |
| 2012/0330351 A1 | 12/2012 | Friedman et al. |
| 2013/0197516 A1* | 8/2013 | Kappel ................ A61B 17/29 606/46 |
| 2014/0135763 A1 | 5/2014 | Kappus et al. |
| 2014/0276797 A1 | 9/2014 | Batchelor et al. |

\* cited by examiner

DEPLOYMENT MECHANISM FOR SURGICAL INSTRUMENTS

BACKGROUND

Technical Field

The present disclosure relates to surgical instruments and, more particularly, to a deployment mechanism for deploying or actuating one or more components of a surgical instrument.

Background of Related Art

Bipolar electrosurgical instruments typically include two generally opposing electrodes charged to different electric potentials to selectively apply energy to tissue. For example, a bipolar electrosurgical forceps utilizes both mechanical clamping action and electrical energy to effect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many forceps have been designed which incorporate a knife or blade member that effectively severs the tissue after forming a tissue seal.

Monopolar surgical instruments, on the other hand, include an active electrode, and are used in conjunction with a remote return electrode, e.g., a return pad, to apply energy to tissue. Monopolar instruments have the ability to rapidly move through tissue and dissect through narrow tissue planes.

In some surgical procedures, it may be beneficial to use both bipolar and monopolar instrumentation, e.g., procedures where it is necessary to dissect through one or more layers of tissue in order to reach underlying tissue(s) to be sealed. Further, it may be beneficial, particularly with respect to endoscopic surgical procedures, to provide a single instrument incorporating both bipolar and monopolar features, thereby obviating the need to alternatingly remove and insert the bipolar and monopolar instruments in favor of one another.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with the present disclosure, a surgical instrument is provided including an energizable member, an end effector assembly, and a deployment mechanism. The energizable member includes a distal tip disposed at a distal end thereof and a proximal hub engaged to a proximal end thereof. The proximal hub is movable between a proximal position and a distal position for moving the energizable member between a storage position and a deployed position relative to the end effector assembly. The deployment mechanism is configured to move the proximal hub between the proximal position and the distal position and includes a rotatable shaft, a cord, a biasing member, and a gear assembly. The cord includes a proximal end engaged to the rotatable shaft and a distal end engaged to the proximal hub. The biasing member is positioned to bias the proximal hub towards the distal position. The gear assembly is operably coupled to the rotatable shaft and configured to move the proximal hub from the distal position to the proximal position against the bias of the biasing member by rotating the rotatable shaft relative to the cord to at least partially wind-up the cord about the rotatable shaft.

In an aspect of the present disclosure, at least one lever is operably coupled to the gear assembly. The at least one lever is rotatable from an actuated position to an un-actuated position to operate the gear assembly to move the proximal hub from the distal position to the proximal position.

In an aspect of the present disclosure, a latching mechanism is provided for releasably latching the one or more levers in the un-actuated position to thereby maintain the proximal hub in the proximal position against the bias of the biasing member.

In another aspect of the present disclosure, the deployment mechanism is configured such that rotation of one of the one or more levers from the un-actuated position further away from the actuated position disengages the latching mechanism allowing the proximal hub to move to the distal position under the bias of the biasing member.

In still another aspect of the present disclosure, the deployment mechanism is configured such that movement of the proximal hub to the distal position under the bias of the biasing member pulls the cord distally to rotate the rotatable shaft relative to the cord to at least partially unwind the cord about the rotatable shaft.

In yet another aspect of the present disclosure, the deployment mechanism is configured such that rotation of the rotatable shaft relative to the cord to at least partially unwind the cord rotates the one or more levers from the un-actuated position to the actuated position.

In still yet another aspect of the present disclosure, the gear assembly includes one or more first gear components and one or more second gear components disposed in meshed engagement with the respective first gear components. The first gear component(s) is coupled to the one or more levers and the second gear component(s) is coupled to the rotatable shaft.

In another aspect of the present disclosure, the deployment mechanism is configured such that rotation of the first gear component(s) in a first direction effects rotation of the second gear component(s) in a second, opposite direction.

In yet another aspect of the present disclosure, the biasing member is disposed within a cartridge and the proximal hub is slidably disposed about the cartridge.

In still another aspect of the present disclosure, an insulative member is engaged to the proximal hub at a proximal end of the insulative member. Movement of the proximal hub between the proximal position and the distal position moves the insulative member between a storage position and a deployed position relative to the end effector assembly.

Another surgical instrument provided in accordance with the present disclosure includes a housing, a shaft extending distally from the housing, an end effector assembly disposed at a distal end of the shaft, a monopolar assembly, and a deployment mechanism. The end effector assembly is adapted to connect to a source of energy for treating tissue with bipolar energy. The monopolar assembly includes a proximal hub disposed within the housing and an energizable member engaged to the proximal hub and extending distally therefrom. The energizable member includes a distal tip adapted to connect to a source of energy for treating tissue with monopolar energy. The proximal hub is movable relative to the housing between a proximal position and a distal position for moving the energizable member between a storage position, wherein the distal tip is positioned adjacent the end effector assembly, and a deployed position, wherein the distal tip extends distally from the end effector assembly. The deployment mechanism is configured to move the proximal hub between the proximal position and the distal position. The deployment mechanism includes a biasing member positioned to bias the proximal hub towards the distal position, a rotatable shaft disposed within the housing, a cord disposed within the housing, and one or more levers rotatably disposed on the housing. The cord includes a proximal end engaged to the rotatable shaft and a distal end engaged to the proximal hub. The one or more levers are operably coupled to the rotatable shaft and are rotatable between an actuated position and an un-actuated position. Rotation of one or more of the one or more levers from the actuated position to the un-actuated position rotates the rotatable shaft relative to the cord to at least partially wind-up the cord about the rotatable shaft, thereby pulling the proximal hub from the proximal position to the distal position against the bias of the biasing member.

In an aspect of the present disclosure, the surgical instrument further includes a gear assembly disposed within the housing. The gear assembly is operably couples between the one or more levers and the rotatable shaft. More specifically, the gear assembly includes one or more first gear components coupled to the one or more levers and one or more second gear components coupled to the rotatable shaft. The first gear component(s) and the second gear component(s) are disposed in meshed engagement with one another.

In another aspect of the present disclosure, the deployment mechanism is configured such that rotation of the first gear component(s) in a first direction effects rotation of the second gear component(s) in a second, opposite direction.

In yet another aspect of the present disclosure, the surgical instrument further includes a latching mechanism configured to releasably latch the one or more levers in the un-actuated position thereby maintaining the proximal hub in the proximal position against the bias of the biasing member.

In still another aspect of the present disclosure, the latching mechanism includes one or more latching tabs coupled to the deployment mechanism and one or more tracks defined on an interior surface of the housing. The latching tab(s) is configured to move along the track(s) to releasably latch the one or more levers in the un-actuated position.

In yet another aspect of the present disclosure, the deployment mechanism is configured such that movement of the proximal hub to the distal position under the bias of the biasing member pulls the cord distally to rotate the rotatable shaft relative to the cord to at least partially unwind the cord about the rotatable shaft.

In still yet another aspect of the present disclosure, the deployment mechanism is configured such that rotation of the rotatable shaft relative to the cord to at least partially unwind the cord rotates the one or more levers from the un-actuated position to the actuated position.

In another aspect of the present disclosure, the biasing member is disposed within a cartridge mounted within the housing and the proximal hub is slidably disposed about the cartridge.

In yet another aspect of the present disclosure, the monopolar assembly further includes an insulative member engaged to the proximal hub at a proximal end of the insulative member. Movement of the proximal hub between the proximal position and the distal position moves the insulative member between a storage position, wherein the insulative member is positioned proximally of the end effector assembly, and a deployed position, wherein the insulative member is disposed about the end effector assembly.

In still another aspect of the present disclosure, the end effector assembly includes first and second jaw members. At least one of the jaw members is movable relative to the other for grasping tissue therebetween. At least one of the jaw members is adapted to connect to a source of energy for treating tissue grasped therebetween.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
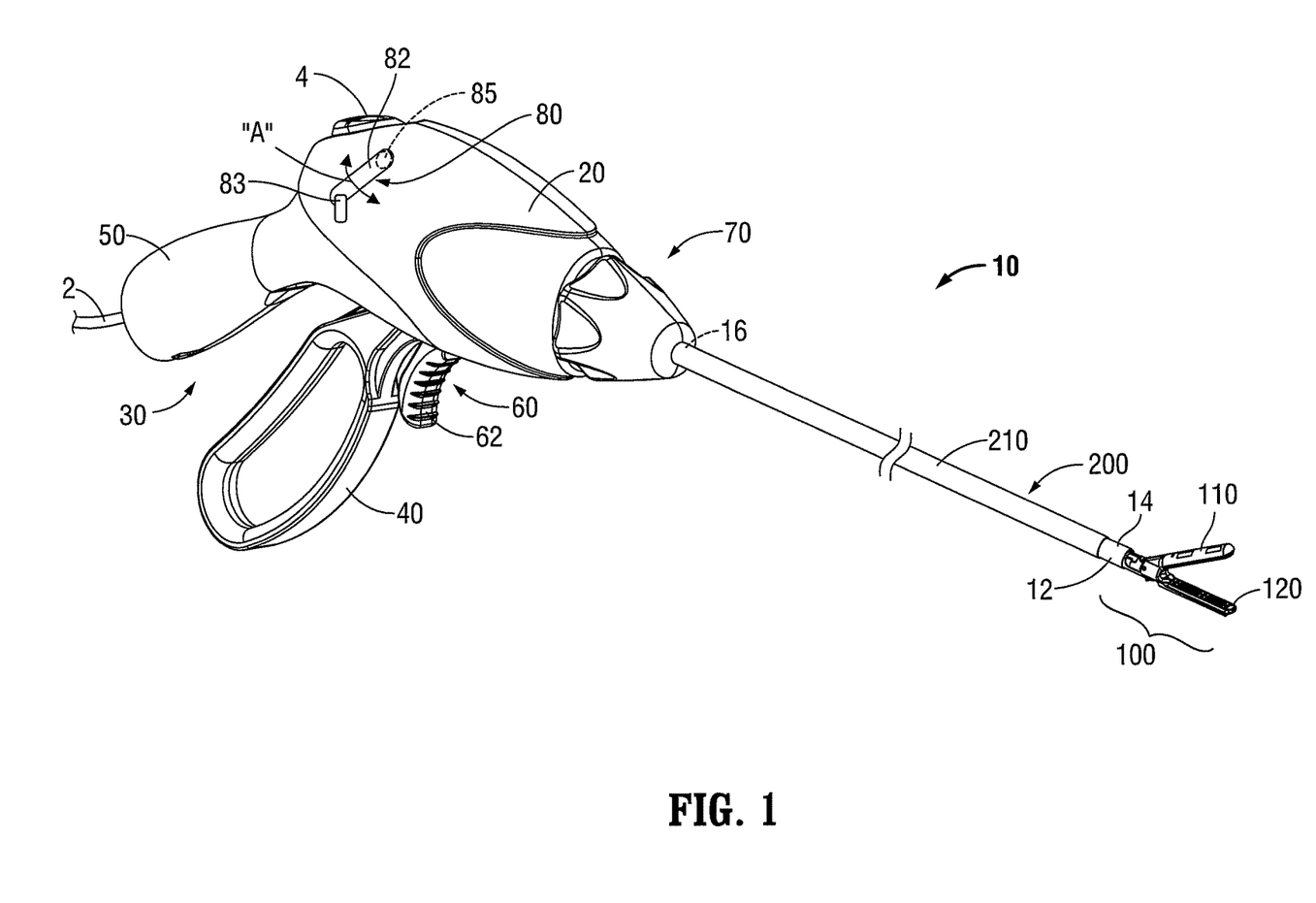
FIG. 1 is a front, perspective view of an endoscopic surgical forceps having a housing and a shaft that extends therefrom for supporting an end effector assembly, in accordance with the present disclosure.
Figure 2:
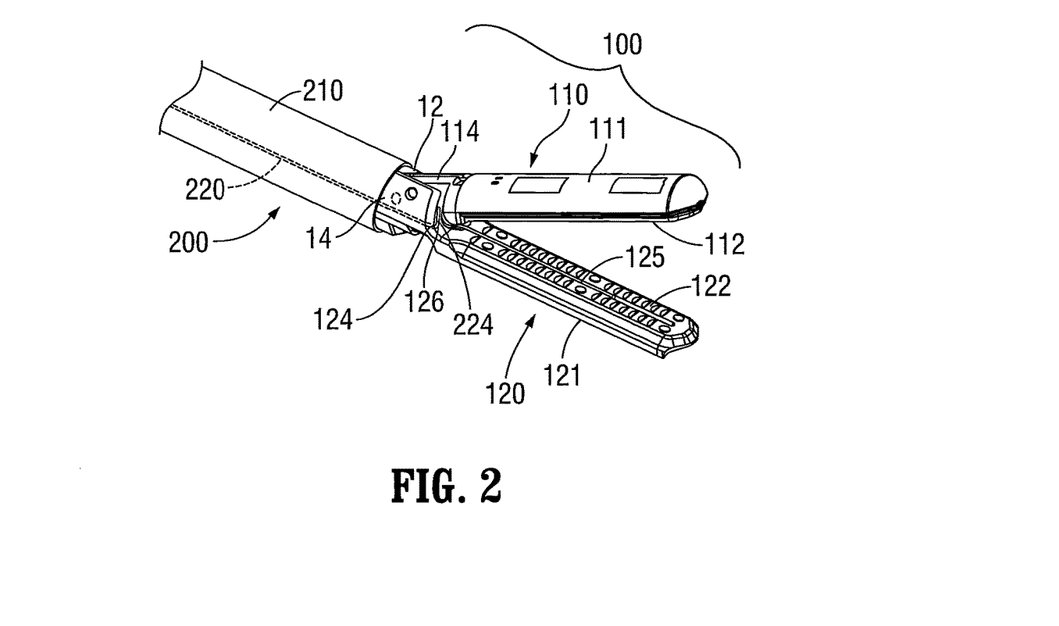
FIG. 2 is an enlarged, front, perspective view of an end effector assembly of the forceps of FIG. 1, wherein jaw members of the end effector assembly are disposed in spaced-apart relation and wherein a monopolar assembly is disposed in a storage condition.

Referring generally to FIGS. 1 and 2, a forceps provided in accordance with the present disclosure is shown generally identified by reference numeral 10. Forceps 10, as will be described below, is configured to operate in both a bipolar mode, e.g., for grasping, treating, and/or dissecting tissue, and a monopolar mode, e.g., for treating and/or dissecting tissue. Although the present disclosure is shown and described with respect to forceps 10, the aspects and features of the present disclosure are equally applicable for use with any suitable surgical instrument or portion(s) thereof for selectively deploying the assemblies and/or components of the surgical instrument. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIGS. 1 and 2, forceps 10 includes a housing 20, a handle assembly 30, a trigger assembly 60, a rotating assembly 70, a deployment mechanism 80, an end effector assembly 100, and a monopolar assembly 200. Forceps 10 further includes a shaft 12 having a distal end 14 configured to mechanically engage end effector assembly 100 and a proximal end 16 that mechanically engages housing 20. Forceps 10 also includes an electrosurgical cable 2 that connects forceps 10 to a generator (not shown) or other suitable energy source, although forceps 10 may alternatively be configured as a battery powered instrument. Cable 2 includes wires (not shown) extending therethrough that have sufficient length to extend through shaft 12 in order to provide electrical energy to at least one electrically-conductive surface 112, 122 (FIG. 2) of jaw members 110, 120, respectively, of end effector assembly 100, e.g., upon activation of activation switch 4 in a bipolar mode. One or more of the wires of cable 2 extends through housing 20 in order to provide electrical energy to monopolar assembly 200, e.g., upon activation of activation switch 4 in a monopolar mode. Rotating assembly 70 is rotatable in either direction to rotate end effector assembly 100 and monopolar assembly 200 relative to housing 20. Housing 20 houses the internal working components of forceps 10. A detailed description of such internal working components, e.g., the drive assembly (not shown), rotating assembly 70, and trigger assembly 60 can be found in U.S. Pat. No. 7,766,910, the entire contents of which are incorporated herein by reference.

Handle assembly 30 includes a movable handle 40 and a fixed handle 50. Fixed handle 50 is integrally associated with housing 20 and movable handle 40 is movable relative to fixed handle 50. Movable handle 40 is movable relative to fixed handle 50 between an initial position, wherein movable handle 40 is spaced from fixed handle 50, and a compressed position, wherein movable handle 40 is compressed towards fixed handle 50. A biasing member (not shown) may be provided to bias movable handle 40 towards the initial position. Movable handle 40 is ultimately connected to a drive assembly (not shown) that, together, mechanically cooperate to impart movement of jaw members 110, 120 between the spaced-apart position, corresponding to the initial position of movable handle 40, and the approximated position, corresponding to the compressed position of movable handle 40. Any suitable drive assembly for this purpose may be provided.

Trigger assembly 60 includes trigger 62 that is operably coupled to a knife assembly (not shown). Trigger 62 is selectively actuatable to advance a knife (not shown) of the knife assembly from a retracted position, wherein the knife is disposed proximally of jaw members 110, 120, to an extended position, wherein the knife extends at least partially between jaw members 110, 120 to cut tissue grasped between jaw members 110, 120. Alternatively or additionally, electrical or electromechanical cutting features may be provided.

Referring to FIG. 2, end effector assembly 100 is attached at distal end 14 of shaft 12 and includes opposing jaw members 110, 120 pivotably coupled to one another. Each of the jaw members 110 and 120 includes a jaw body 111, 121 supporting the respective electrically-conductive surface 112, 122, and a respective proximally-extending jaw flange 114, 124. Flanges 114, 124 are pivotably coupled to one another to permit movement of jaw members 110, 120 relative to one another between a spaced-apart position (FIG. 2) and an approximated position (FIG. 3) for grasping tissue between surfaces 112, 122. One or both of surfaces 112, 122 are adapted to connect to the energy source, e.g., via the wires of cable 2 (FIG. 1), and are configured to conduct energy through tissue grasped therebetween to treat, e.g., seal, tissue. More specifically, in some embodiments, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating e.g., sealing, tissue. Activation switch 4 (FIG. 1) is operably coupled between the energy source and surfaces 112, 122, thus allowing the user to selectively apply energy to surfaces 112, 122 of jaw members 110, 120, respectively, of end effector assembly 100 during a bipolar mode of operation.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments, a knife channel 125 may be defined within one or both of jaw members 110, 120 to permit reciprocation of the knife therethrough, e.g., upon actuation of a trigger 62 of trigger assembly 60, to cut tissue grasped between jaw members 110, 120. Alternatively or additionally, as noted above, electrical cutting mechanisms may be provided for electrically or electromechanically cutting tissue grasped between jaw members 110, 120.

Figure 3:
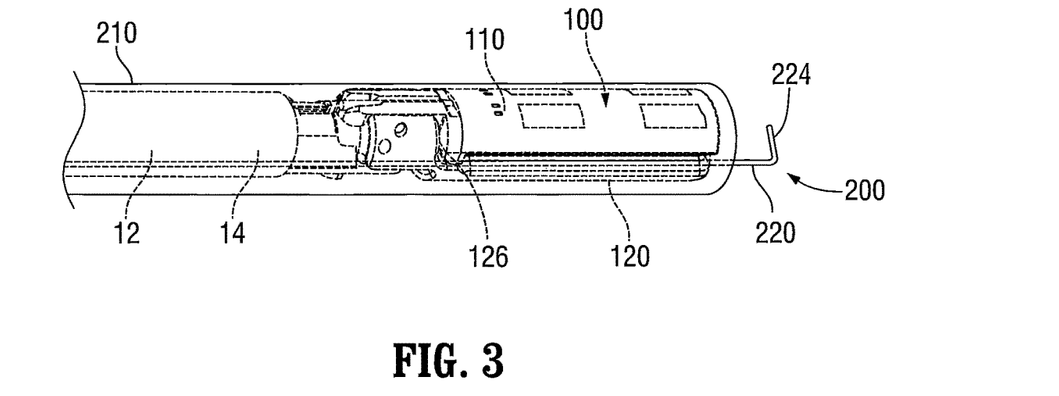
FIG. 3 is an enlarged, side, perspective view of the end effector assembly of FIG. 2 (shown in phantom), wherein the jaw members are disposed in approximated relation and wherein the monopolar assembly is disposed in a deployed condition.
Figure 4A:
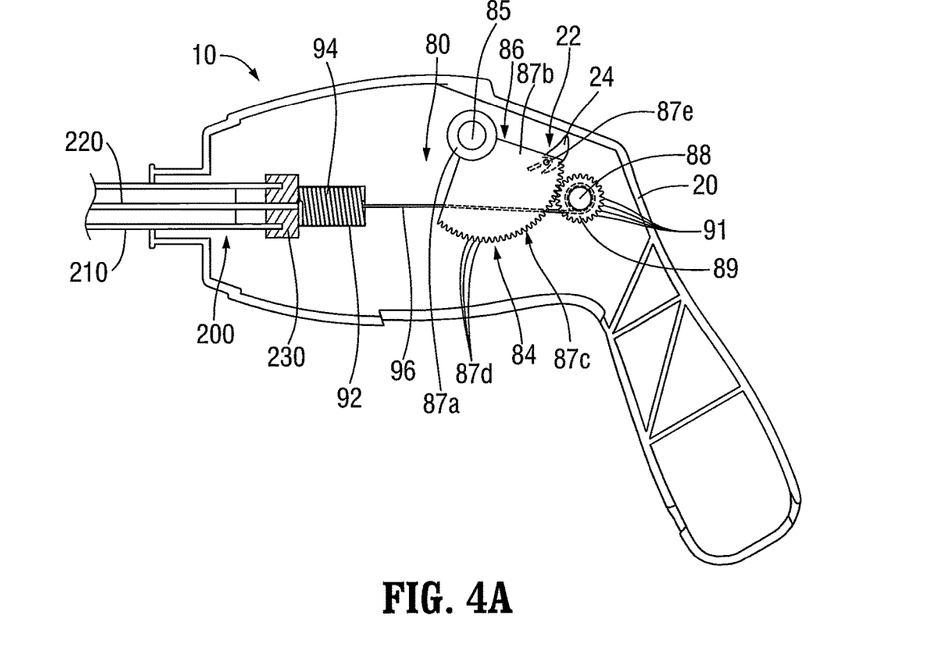
FIG. 4A is a side, cut-a-way view of the housing of the forceps of FIG. 1 showing a deployment mechanism configured to selectively deploy the monopolar assembly from the storage condition.

Referring to FIGS. 1-3, monopolar assembly 200 generally includes an insulative sleeve 210, an energizable rod member 220, and a proximal bushing 230 (FIG. 4A). Insulative sleeve 210 is slidably disposed about shaft 12 and is selectively movable about and relative to shaft 12 and end effector assembly 100 between a storage position (FIG. 2), wherein insulative sleeve 210 is disposed proximal to end effector assembly 100, and a deployed position (FIG. 3), wherein insulative sleeve 210 is substantially disposed about end effector 100 so as to electrically insulate surfaces 112, 122 of jaw members 110, 120, respectively, during monopolar activation.

Energizable rod member 220 extends through sleeve 210 and distally therefrom, ultimately defining an electrically-conductive distal tip 224. Energizable rod member 220 and, more specifically, distal tip 224 thereof, functions as the active electrode of monopolar assembly 200. The one or more wires (not shown) extending from cable 2 through housing 20 (see FIG. 1), are coupled to energizable rod member 220 to provide energy to energizable rod member 220, e.g., upon actuation of activation switch 4 (FIG. 1), for treating tissue in a monopolar mode of operation. Energizable rod member 220 is movable between a storage position (FIG. 2), wherein distal tip 224 of rod member 220 is positioned adjacent proximal flange 124 of jaw member 120, and a deployed position (FIG. 3), wherein distal tip 224 of rod member 220 extends distally from the distal ends of jaw members 110, 120. Distal tip 224 may be hook-shaped (as shown), or may define any other suitable configuration, e.g., linear, circular, angled, etc.

In the storage position of energizable rod member 220, as shown in FIG. 2, distal tip 224 is disposed within an insulated groove 126 defined within proximal flange 124 of jaw member 120, although other configurations are also contemplated. Insulated groove 126 electrically-insulates distal tip 224 of rod member 220 from electrically-conductive surfaces 112, 122 of jaw members 110, 120, respectively, and from surrounding tissue when disposed in the storage position. Alternatively, distal tip 224 may only be insulated from surface 112. In such configurations, distal tip 224 of rod member 220 is capable of being energized to the same polarity as surface 122. In the extended position of energizable rod member 220, as shown in FIG. 3, distal tip 224 extends distally from end effector assembly 100 and insulative sleeve 210, which substantially surrounds end effector assembly 100. In this position, energy may be applied to distal tip 224 of rod member 220 to treat tissue, e.g., via activation of activation switch 4 (FIG. 1), in the monopolar mode of operation.

Figure 4B:
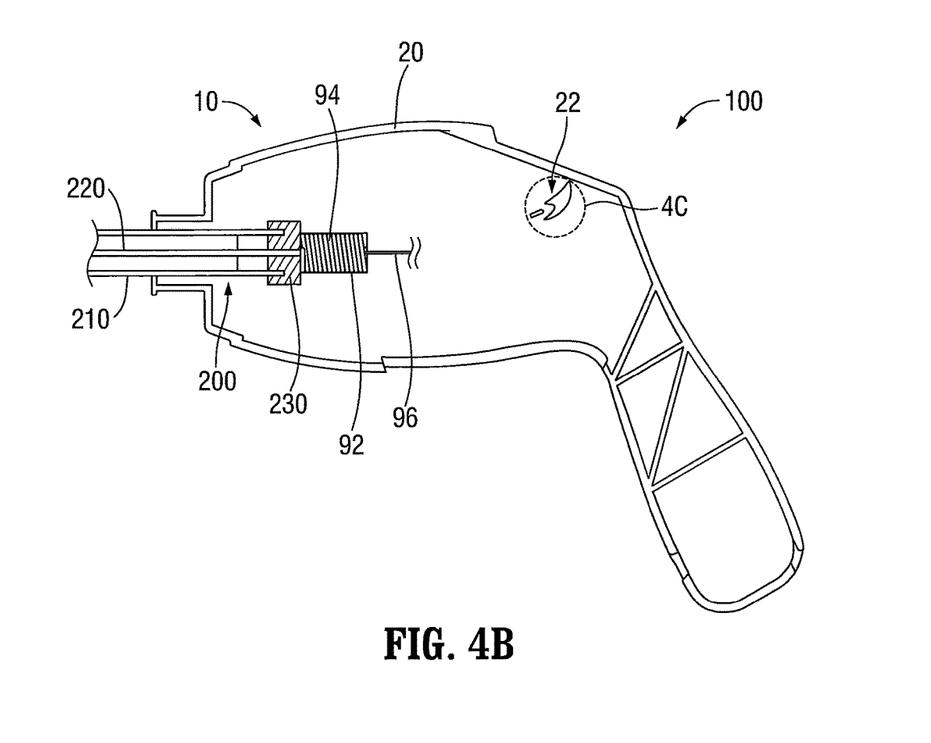
FIG. 4B is a side, cut-a-way view of the housing of the forceps of FIG. 1 with a proximal portion of the deployment mechanism removed.
Figure 4C:
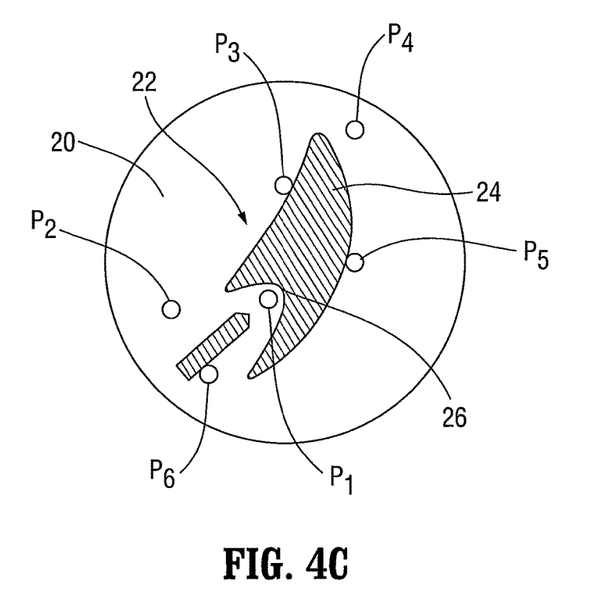
FIG. 4C is an enlarged view of the area of detail indicated as "4C" in FIG. 4B.
Figure 5:
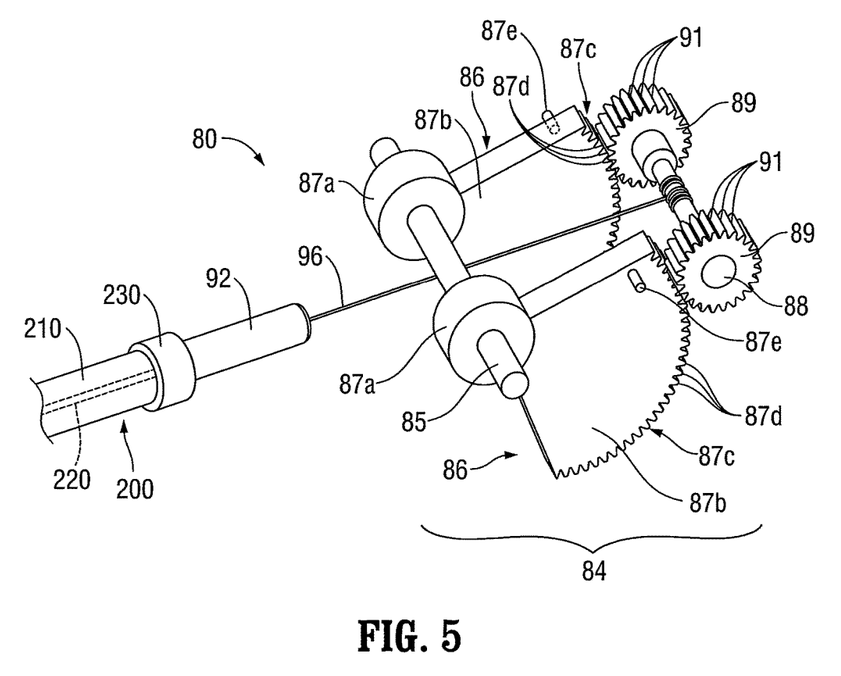
FIG. 5 is an enlarged, front, perspective view of the deployment mechanism of FIG. 4A.
Figure 6A:
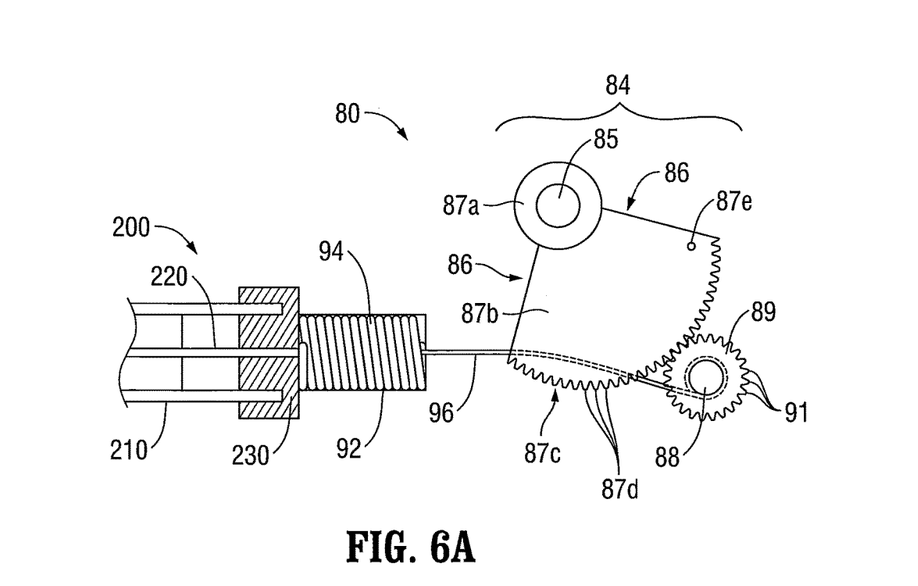
FIG. 6A is an enlarged, side view of the deployment mechanism and a proximal end of the monopolar assembly, wherein the deployment mechanism is disposed in an un-actuated position corresponding to the storage condition of the monopolar assembly.
Figure 6B:
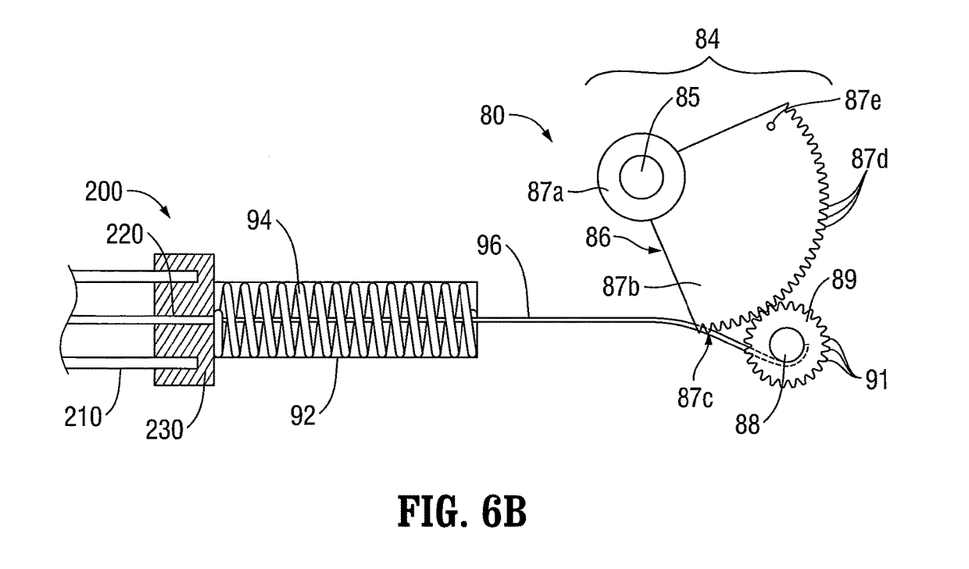
FIG. 6B is a side view of the deployment mechanism and the proximal end of the monopolar assembly, wherein the deployment mechanism is disposed in an actuated position corresponding to the condition of the monopolar assembly.

Referring additionally to FIGS. 4A-6B, proximal bushing 230 is engaged to both the proximal end of sleeve 210 and the proximal end of energizable rod member 220, thereby coupling sleeve 210 and energizable rod member 220 to one another. As such, sleeve 210 and energizable rod member 220 move between their respective storage positions (FIGS. 2 and 6A), e.g., the storage condition of monopolar assembly 200, and their deployed positions (FIGS. 3 and 6B), e.g., the deployed condition of monopolar assembly 200, upon selective translation of proximal bushing 230. As detailed below, proximal bushing 230 is operably coupled to deployment mechanism 80 (FIG. 4A) for selectively translating proximal bushing 230 and, thus, for selectively transitioning monopolar assembly 200 between the storage condition (FIGS. 2 and 6A) and the deployed condition (FIGS. 3 and 6B). In some embodiments, insulative sleeve 210 is not provided and, thus, only energizable rod member 220 is utilized. In such embodiments, the configuration and use of monopolar assembly 200 and deployment mechanism 80 (FIG. 4A) are substantially similar as detailed herein, with the exception of insulative sleeve 210 being omitted. Alternatively, insulative sleeve 210 may be independently deployed, e.g., via a separate mechanism (not shown).

With reference to FIGS. 4A-6B, in conjunction with FIG. 1, as mentioned above, deployment mechanism 80 is operably coupled to monopolar assembly 200 for selectively transitioning monopolar assembly 200 between the storage condition (FIGS. 2 and 6A) and the deployed condition (FIGS. 3 and 6B). Deployment mechanism 80 generally includes a pair of levers 82 (FIG. 1; only one lever 82 is shown), a gear assembly 84, a cartridge 92, a biasing member 94, and a cord 96.

Gear assembly 84 includes a bar 85 that extends transversely through housing 20 and outwardly from each side of housing 20. Bar 85 is rotatably coupled to housing 20. Levers 82 are engaged to the portions of bar 85 that extend from housing 20 on either side thereof, thus enabling selective actuation of deployment mechanism 80 from either side of housing 20. Each lever 82 may further include a finger tab 83 (FIG. 1) provided at an opposite end of the lever 82 as compared to bar 85 so as to facilitate rotation of lever 82 and, thus, corresponding rotation of bar 85 relative to housing 20. Levers 82, as shown in FIG. 1, are rotatable relative to housing 20 along the path indicated by arrows "A," between an un-actuated position (as shown in FIG. 1) corresponding to the storage condition of monopolar assembly 200 (FIGS. 2 and 6A), and an actuated position corresponding to the deployed condition of monopolar assembly 200 (FIGS. 3 and 6B).

With particular reference to FIGS. 4A and 5 (levers 82 have been removed from FIG. 5 so as not to obscure the other components of deployment mechanism 80), gear assembly 84 further includes a pair of first gear components, e.g., gear plates 86, disposed within housing 20 and coupled to bar 85 towards the respective ends thereof. Each gear plate 86 includes a base 87a that is engaged about bar 85 and a gear body 87b extending proximally from its respective base 87a. Each gear body 87b defines an arcuate engagement surface 87c having a plurality of gear teeth 87d formed thereon. With levers 82 (FIG. 1) engaged to bar 85 and gear plates 86 likewise engaged to bar 85, rotation of either or both of levers 82 relative to housing 20 (see FIG. 1) effects similar rotation of bar 85 and, thus, gear plates 86.

Each gear body 87b further includes a resiliently flexible latching tab 87e, extending laterally outwardly therefrom towards a respective inner surface of housing 20. Referring additionally to FIGS. 4B-4C, the latching tab 87e of each gear body 87b is operably associated with a corresponding track 22 defined on an inner surface of housing 20 (only one of tracks 22 is shown in FIGS. 4B-4C). More specifically, latching tabs 87e and tracks 22 cooperate to releasably latch levers 82 (FIG. 1) in the un-actuated position (as shown in FIG. 1) corresponding to the storage condition of monopolar assembly 200 (FIGS. 2 and 6A). The configurations and functions of latching tabs 87e and tracks 22 are detailed below with respect to the use and operation of forceps 10 (FIG. 1). Other suitable latching mechanisms are also contemplated. Further, a latching mechanism (not shown) may also be provided for releasably latching monopolar assembly 200 in the deployed condition (FIGS. 3 and 6B).

With reference again to FIGS. 4A and 5, gear assembly 84 further includes a shaft 88 transversely disposed and rotatably mounted within housing 20 (see FIG. 4A). Shaft 88 includes a pair of second gear components, e.g., first and second annular gears 89, engaged about shaft 88 towards the respective ends thereof. Each annular gear 89 defines a plurality of circumferentially-disposed gear teeth 91 and is positioned such that gear teeth 91 are disposed in meshed engagement with the respective gear teeth 87d of the corresponding gear plate 86. As a result of this meshed engagement, rotation of either or both of levers 82 relative to housing 20 (see FIG. 1) in a first direction effects rotation of shaft 88 in an opposite direction. That is, clockwise rotation of either of levers 82 relative to housing 20 see (FIG. 1) effects counter-clockwise rotation of shaft 88 relative to housing 20 (see FIG. 1), and vice versa.

Continuing with reference to FIGS. 4A and 5, cord 96 is engaged to shaft 88 at the proximal end of cord 96 and extends distally from shaft 88, through cartridge 92, ultimately engaging proximal bushing 230 of monopolar assembly 200 at the distal end of cord 96. Cord 96 may be made from any suitable material and/or mechanisms that form a flexible linkage, e.g., rope, wire, chain, etc. The flexible linkage between gear assembly 84 and proximal bushing 230 formed by cord 96 is advantageous in that it allows gear assembly 84 and proximal bushing 230 to be spaced-apart from one another, offset relative to one another, and/or have other components disposed therebetween without requiring complex linkage(s) joining gear assembly 84 and proximal bushing 230. Further, various pulley components (not explicitly shown) may be utilized to route cord 96 over/ under and around various different components, thus providing additional flexibility with respect to positioning of the various components disposed within housing 20.

Cartridge 92 is mounted within housing 20 and houses biasing member 94, e.g., a coil spring, that is interdisposed between the proximal end of cartridge 92 and proximal bushing 230. Proximal bushing 230 is slidably disposed about cartridge 92 and is biased distally relative to cartridge 92 via biasing member 94. This distal biasing of proximal bushing 230 biases monopolar assembly 200 towards the deployed condition (FIGS. 3 and 6B). Further, as a result of the distal biasing of proximal bushing 230, cord 96 is likewise biased distally such that shaft 88 is rotationally biased in a clockwise direction (as viewed in FIG. 4A) and gear plates 86 and levers 82 (FIG. 1) are rotationally biased in a counter-clockwise direction (as viewed in FIG. 4A). As detailed below, latch tabs 87e and tracks 22 cooperate to releasably latch monopolar assembly 200 in the storage condition (FIGS. 2 and 6A) despite this bias towards the deployed condition (FIGS. 3 and 6B). Once monopolar assembly 200 has been deployed, rotation of either or both of levers 82 (FIG. 1) against the bias of biasing member 94 effects rotation of shaft 88 in a counter-clockwise direction (as viewed in FIG. 4A) to wind up cord 96 about shaft 88, thereby pulling proximal bushing 230 proximally against the bias of biasing member 94 to return monopolar assembly 200 towards the storage condition (FIGS. 2 and 6A), as will be detailed below.

Referring to FIGS. 1-6B, the use and operation of forceps 10 in both the bipolar mode, e.g., for grasping, treating, and/or cutting tissue, and the monopolar mode, e.g., for electrical/electromechanical tissue treatment (or to perforate or score tissue without the use of energy), is described.

With respect to the bipolar mode of operation, monopolar assembly 200 is maintained in the storage condition (FIGS. 2 and 6A). That is, referring to FIGS. 1-2, 4C and 6A, for use in the bipolar mode of operation, levers 82 remain disposed in the un-actuated position (as shown in FIG. 1) with latching tabs 87e engaged within saddles 26 of stop members 24 of tracks 22 at position $P_1$ (FIG. 4C). In this position, latching tabs 87e are maintained in a flexed condition, e.g., flexed from their neutral positions, under the urging of stop members 24, the importance of which will be detailed below. Engagement of latching tabs 87e within saddles 26 inhibits rotation of gear bodies 87b, thus inhibiting rotation of shaft 88 and distal translation of cord 96. As such, with latching tabs 87e engaged within saddles 26 at position $P_1$, monopolar assembly 200 is retained in the storage condition (FIG. 2) despite biasing member 94 acting to bias monopolar assembly 200 towards the deployed condition (see FIG. 6B). In this latched condition, as shown in FIG. 6A, biasing member 94 is disposed in a tensioned state, e.g., storing potential energy, and cord 96 is wound-up about shaft 88.

For use in the bipolar mode of operation, with jaw members 110, 120 initially disposed in the spaced-apart position (FIG. 2), end effector assembly 100 may be maneuvered into position such that tissue to be grasped, treated, e.g., sealed, and/or cut, is disposed between jaw members 110, 120. Next, movable handle 40 is depressed, or pulled proximally relative to fixed handle 50 such that jaw member 110 is pivoted relative to jaw member 120 from the spaced-apart position to the approximated position to grasp tissue therebetween. In this approximated position, energy may be supplied, e.g., via activation of switch 4, to electrically-conductive surface 112 of jaw member 110 and/or electrically-conductive surface 122 of jaw member 120 and conducted through tissue to treat tissue, e.g., to effect a tissue seal or otherwise treat tissue in the bipolar mode of operation.

Once tissue treatment is complete (or to cut untreated tissue), the knife (not shown) may be deployed from within shaft 12 to between jaw members 110, 120, e.g., via actuation of trigger 62 of trigger assembly 60, to cut tissue grasped between jaw members 110, 120. When tissue treatment and/or cutting are complete, jaw members 110, 120 may be returned to the spaced-apart position to release the treated and/or divided tissue.

Referring to FIGS. 1, 4C and 6A-6B, for use of forceps 10 in the monopolar mode of operation, monopolar assembly 200 is unlatched and deployed to the deployed condition (FIGS. 3 and 6B). In order to unlatch levers 82 to deploy monopolar assembly 200 (FIGS. 2-3), either or both levers 82 are rotated away from, e.g., in an opposite direction from, the actuated position sufficiently so as to move latching tabs 87e to position $P_2$. At position $P_2$, latching tabs 87e are spaced-apart from stop members 24 such that latching tabs 87e are permitted to resiliently return to their neutral, e.g., unflexed, positions, wherein latching tabs 87e are offset from stop members 24. The return of latching tabs 87e to their neutral positions upon movement of latching tabs 87e from position $P_1$ to position $P_2$ inhibits re-engagement of latching tabs 87e within saddles 26 once position $P_2$ has been achieved. Thus, with latching tabs 87e disposed at position $P_2$, lever(s) 82 may be released. Upon release of lever(s) 82, the potential energy stored in biasing member 94 is converted into potential energy to urge proximal bushing 230 distally to thereby push insulative sleeve 210 and energizable rod member 220 distally from their respective storage positions to their respective deployed positions (FIGS. 3 and 6B). As proximal bushing 230 is translated distally, cord 96 is likewise pulled distally. This distal pulling of cord 96 unwinds cord 96 from about shaft 88 and urges shaft 88 to rotate in the clockwise direction (as viewed in FIG. 4A) to the position shown in FIG. 6B. Rotation of shaft 88 in the clockwise direction, in turn, rotates gear bodies 87b, bar 85 and, thus, levers 82 (FIG. 1) in the counter-clockwise direction (as viewed in FIG. 4A) until levers 82 (FIG. 1) reach the actuated position corresponding to the deployed condition of monopolar assembly 200 (FIGS. 3 and 6B). As can be appreciated, monopolar assembly 200 (FIG. 3) is deployed under the bias of biasing member 94 and, thus, requires minimal force by the user, e.g., only the force required to move lever(s) 82 to disengage latching tabs 87e from saddles 26 of stop members 24.

Referring to FIGS. 1, 4C, and 6B, the rotation of gear bodies 87b under the bias of biasing member 94 as monopolar assembly 200 is deployed moves latching tabs 87e from position $P_2$ through position $P_3$, wherein latching tabs 87e contact stop members 24 and are flexed from their neutral positions by stop members 24 before reaching position $P_4$, corresponding to the deployed condition of monopolar assembly 200 (FIG. 3). At position $P_4$, latching tabs 87e are no longer urged to flex from their neutral positions by stop members 24 and, thus, are resiliently returned to their neutral positions. This configuration, similarly as above, inhibits latching tabs 87e from returning back to positions $P_2$ and $P_3$ in the opposite direction.

In the deployed condition of monopolar assembly 200, as shown in FIG. 3 and as mentioned above, insulative sleeve 210 surrounds jaw members 110, 120 and energizable rod member 220 extends distally from end effector assembly 100 and insulative sleeve 210. With monopolar assembly 200 disposed in this deployed condition, activation switch 4 may be actuated to supply energy to energizable rod member 220 to treat, e.g., dissect, tissue. During application of energy to tissue via energizable rod member 220, forceps 10 may be moved relative to tissue, e.g., longitudinally, transversely, and/or radially, to facilitate electromechanical treatment of tissue.

At the completion of tissue treatment, e.g., dissection, monopolar assembly 200 may be returned to the storage condition (FIGS. 2 and 6A). More specifically, with reference to FIGS. 1 and 4C-6B, in order to return monopolar assembly 200 to the storage condition, either or both of levers 82 (FIG. 1) are rotated back towards the un-actuated position against the bias of biasing member 94. This rotation of levers 82 (FIG. 1) effects rotation of shaft 88 in a clockwise direction (as viewed in FIG. 4A) to wind up cord 96 about shaft 88, thereby pulling proximal bushing 230 proximally against the bias of biasing member 94 and, as a result, pulling insulative sleeve 210 and energizable rod member 220 proximally from their respective deployed positions to their respective storage positions (FIGS. 3 and 6A).

As monopolar assembly 200 is returned to the storage condition, latching tabs 87e are moved along tracks 22 from position $P_4$ through position $P_5$, wherein latching tabs 87e contact stop members 24 and are flexed from their neutral positions by stop members 24. Upon once again reaching the un-actuated position of levers 82 (FIG. 1) corresponding to the storage condition of monopolar assembly 200, latching tabs 87e are positioned beyond stop members 24 at position $P_6$, wherein latching tabs 87e are permitted to resiliently return to their neutral positions. This configuration enables latching tabs 87e to move into engagement within saddles 26 of stop members 24, e.g., returning to position $P_1$, upon release of levers 82 (FIG. 1). Thus, monopolar assembly 200 is one again latched in the storage condition, as shown in FIGS. 2 and 6A.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   an end effector assembly;
   an energizable member including a distal tip disposed at a distal end thereof and a proximal hub engaged to a proximal end thereof, the proximal hub movable between a proximal position and a distal position for moving the energizable member between a storage position and a deployed position relative to the end effector assembly; and
   a deployment mechanism configured to move the proximal hub between the proximal position and the distal position, the deployment mechanism including:
   a rotatable shaft;
   a cord including a proximal end engaged to the rotatable shaft and a distal end engaged to the proximal hub;
   a biasing member positioned to bias the proximal hub towards the distal position, the biasing member disposed within a cartridge mounted within the housing and the proximal hub slidably disposed about the cartridge; and
   a gear assembly operably coupled to the rotatable shaft and configured to move the proximal hub from the distal position to the proximal position against the bias of the biasing member by rotating the rotatable shaft relative to the cord to at least partially wind-up the cord about the rotatable shaft.

2. The surgical instrument according to claim 1, further comprising at least one lever operably coupled to the gear assembly, the at least one lever rotatable from an actuated position to an un-actuated position to operate the gear assembly to move the proximal hub from the distal position to the proximal position.

3. The surgical instrument according to claim 2, further comprising a latching mechanism configured to releasably latch the at least one lever in the un-actuated position thereby maintaining the proximal hub in the proximal position against the bias of the biasing member.

4. The surgical instrument according to claim 3, wherein the deployment mechanism is configured such that rotation of the at least one lever from the un-actuated position away from the actuated position disengages the latching mechanism allowing the proximal hub to move to the distal position under the bias of the biasing member.

5. The surgical instrument according to claim 4, wherein the deployment mechanism is configured such that movement of the proximal hub to the distal position under the bias of the biasing member pulls the cord distally to rotate the rotatable shaft relative to the cord to at least partially unwind the cord about the rotatable shaft.

6. The surgical instrument according to claim 5, wherein the deployment mechanism is configured such that rotation of the rotatable shaft relative to the cord to at least partially unwind the cord rotates the at least one lever from the un-actuated position to the actuated position.

7. The surgical instrument according to claim 1, wherein the gear assembly includes at least one first gear component and at least one second gear component disposed in meshed engagement with the at least one first gear component, the at least one second gear component coupled to the rotatable shaft.

8. The surgical instrument according to claim 7, wherein the deployment mechanism is configured such that rotation of the at least one first gear component in a first direction effects rotation of the at least one second gear component in a second, opposite direction.

9. The surgical instrument according to claim 1, further comprising an insulative member engaged to the proximal hub at a proximal end of the insulative member, wherein movement of the proximal hub between the proximal position and the distal position moves the insulative member between a storage position and a deployed position relative to the end effector assembly.

10. A surgical instrument, comprising:
    a housing;
    a shaft extending distally from the housing;
    an end effector assembly disposed at a distal end of the shaft, the end effector assembly adapted to connect to a source of energy for treating tissue with bipolar energy;
    a monopolar assembly including a proximal hub disposed within the housing and an energizable member engaged to the proximal hub and extending distally therefrom, the energizable member including a distal tip adapted to connect to a source of energy for treating tissue with monopolar energy, the proximal hub movable relative to the housing between a proximal position and a distal position for moving the energizable member between a storage position, wherein the distal tip is positioned adjacent the end effector assembly, and a deployed position, wherein the distal tip extends distally from the end effector assembly; and a deployment mechanism configured to move the proximal hub between the proximal position and the distal position, the deployment mechanism including:
 a biasing member positioned to bias the proximal hub towards the distal position, the biasing member disposed within a cartridge mounted within the housing and the proximal hub slidably disposed about the cartridge;
 a rotatable shaft disposed within the housing;
 a cord disposed within the housing, the cord including a proximal end engaged to the rotatable shaft and a distal end engaged to the proximal hub; and
 at least one lever rotatably disposed on the housing and operably coupled to the rotatable shaft, the at least one lever rotatable between an actuated position and an un-actuated position, wherein rotation of the at least one lever from the actuated position to the un-actuated position rotates the rotatable shaft relative to the cord to at least partially wind-up the cord about the rotatable shaft, thereby pulling the proximal hub from the proximal position to the distal position against the bias of the biasing member.

11. The surgical instrument according to claim 10, further comprising a gear assembly disposed within the housing, the gear assembly operably coupling the at least one lever and the rotatable shaft, the gear assembly including at least one first gear component coupled to the at least one lever and at least one second gear component coupled to the rotatable shaft, the at least one first and second gear components disposed in meshed engagement with one another.

12. The surgical instrument according to claim 11, wherein the deployment mechanism is configured such that rotation of the at least one first gear component in a first direction effects rotation of the at least one second gear component in a second, opposite direction.

13. The surgical instrument according to claim 10, further comprising a latching mechanism configured to releasably latch the at least one lever in the un-actuated position thereby maintaining the proximal hub in the proximal position against the bias of the biasing member.

14. The surgical instrument according to claim 13, wherein the latching mechanism includes at least one latching tab coupled to the deployment mechanism and at least one track defined on an interior surface of the housing, the at least one latching tab configured to move along the at least one track to releasably latch the at least one lever in the un-actuated position.

15. The surgical instrument according to claim 10, wherein the deployment mechanism is configured such that movement of the proximal hub to the distal position under the bias of the biasing member pulls the cord distally to rotate the rotatable shaft relative to the cord to at least partially unwind the cord about the rotatable shaft.

16. The surgical instrument according to claim 15, wherein the deployment mechanism is configured such that rotation of the rotatable shaft relative to the cord to at least partially unwind the cord rotates the at least one lever from the un-actuated position to the actuated position.

17. The surgical instrument according to claim 10, wherein the monopolar assembly further includes an insulative member engaged to the proximal hub at a proximal end of the insulative member, wherein movement of the proximal hub between the proximal position and the distal position moves the insulative member between a storage position, wherein the insulative member is positioned proximally of the end effector assembly, and a deployed position, wherein the insulative member is disposed about the end effector assembly.

18. The surgical instrument according to claim 10, wherein the end effector assembly includes first and second jaw members, at least one of the jaw members movable relative to the other for grasping tissue therebetween, at least one of the jaw members adapted to connect to a source of energy for treating tissue grasped therebetween.

* * * * *